(12) United States Patent
Bhat

(10) Patent No.: US 9,907,803 B2
(45) Date of Patent: Mar. 6, 2018

(54) METHODS FOR TREATING ATTENTION DEFICIT HYPERACTIVITY DISORDER

(71) Applicant: REVIVA PHARMACEUTICALS, INC., Santa Clara, CA (US)

(72) Inventor: Laxminarayan Bhat, Cupertino, CA (US)

(73) Assignee: REVIVA PHARMACEUTICALS, INC., Sunnyvale, CA (US)

( * ) Notice: Subject to any disclaimer, the term of this patent is extended or adjusted under 35 U.S.C. 154(b) by 0 days.

(21) Appl. No.: 15/284,826

(22) Filed: Oct. 4, 2016

(65) Prior Publication Data
US 2017/0035772 A1 Feb. 9, 2017

Related U.S. Application Data

(63) Continuation of application No. PCT/US2015/024976, filed on Apr. 8, 2015.

(60) Provisional application No. 61/977,025, filed on Apr. 8, 2014.

(51) Int. Cl.
A61K 31/495 (2006.01)
A61K 31/496 (2006.01)
A61K 31/535 (2006.01)
A61K 31/5355 (2006.01)
A61K 31/538 (2006.01)

(52) U.S. Cl.
CPC .......... A61K 31/538 (2013.01); A61K 31/495 (2013.01); A61K 31/496 (2013.01); A61K 31/535 (2013.01); A61K 31/5355 (2013.01)

(58) Field of Classification Search
CPC .. A61K 31/538; A61K 31/495; A61K 31/496; A61K 31/535; A61K 31/5355
See application file for complete search history.

(56) References Cited

U.S. PATENT DOCUMENTS

| 8,188,076 | B2 | 5/2012 | Bhat et al. |
| 2002/0052373 | A1 | 5/2002 | Zorn et al. |
| 2004/0048869 | A1 | 3/2004 | Chappell et al. |
| 2009/0023712 | A1* | 1/2009 | Ferger ................. A61K 31/496 514/220 |

OTHER PUBLICATIONS

International Search Report dated Aug. 25, 2015 of PCT Application No. PCT/US2015/024976, filed Apr. 8, 2015 (1 page).
PubChem, Compound Summary for CID 9968343, CHEMBL 150181, Create Date: Oct. 25, 2006. [retrieved on May 14, 2015]. Retrieved from the Internet URL:http://pubchem.ncbi.nim.nih.gov/compound/CID9968343 entire document.
Avale, et al., The dopamine D4 receptor is essential for hyperactivity and impaired behavioral inhibition in a mouse model of attention deficit/hyperactivity disorder. Molecular psychiatry 9(7):18-726, 2004, entire document.
Reviva Pharmaceuticals Reports Positive Top-Line Results from a Phase 2 Clinical Trial of RP5063 for the Treatment of Schizophrenia and Schizoaffective Disorder (Business Wire) (Apr. 9, 2013) (2 pages).

* cited by examiner

Primary Examiner — Yong Chong
(74) Attorney, Agent, or Firm — Perkins Coie LLP; Viola T. Kung

(57) ABSTRACT

The present invention provides a method of using arylpiperazine derivatives for treating attention deficit hyperactivity disorder (ADHD). The method comprises a step of administering to a patient in need thereof an effective amount of a compound of Formula 1, which is an arylpiperazine derivative.

15 Claims, No Drawings

METHODS FOR TREATING ATTENTION DEFICIT HYPERACTIVITY DISORDER

This application is a continuation of PCT/US2015/024976, filed Apr. 8, 2015, which claims priority of U.S. Provisional Application No. 61/977,025, filed Apr. 8, 2014. The contents of the above-identified applications are incorporated herein by reference in their entirety.

TECHNICAL FIELD

The present invention relates to methods of utilizing arylpiperazine derivatives for treating attention deficit hyperactivity disorder.

BACKGROUND

The primary symptoms of attention deficit disorder (ADD)/attention deficit hyperactivity disorder (ADHD) include a persistent pattern of inattention, hyperactivity, and/or impulsivity. The symptoms can appear individually, or in combination (Grohol, J., 2007). The disorder is diagnosed using the American Psychiatric Association: Diagnostic and Statistical Manual of Mental Disorders, Fifth Edition (DSM-5, 2013). In order for a person to qualify as having ADD/ADHD, they must have had symptoms evident before age 12. However, children do not "grow out of" the disorder; it affects both children and adults. According to the DSM-5 criteria, an adult must meet 5 or more and a child must meet 6 or more of the symptoms for at least 6 months to qualify as having ADD/ADHD. The disorder has a negative impact on the affected person's social, academic, and occupational functioning. In addition, 20%-30% of children with ADD/ADHD also have a learning disability, including dyslexia (Martin, B., 2007). Other people with ADD/ADHD have associated conditions such as Tourette's Syndrome, oppositional defiant disorder, conduct disorder, anxiety, depression, or bipolar disorder.

There are many theories regarding the cause of ADD/ADHD. It has a strong genetic basis. The primary genes involved with the cause of ADHD are involved with the brain's ability to produce dopamine, as people with ADD/ADHD typically have decreased levels of dopamine in the brain. Some experts believe that some food additives and sugar exacerbate the condition. However, sugar is not a primary cause of the disorder. Other research indicates that a lack of omega-3 fatty acids (which are important for brain development and function) may be causal of ADD/ADHD symptoms. The addition of fish oil supplements appear to alleviate the disease symptoms in some children, and may boost their scholastic performance. Other factors considered causal for ADD/ADHD include maternal smoking. Women who suffer from ADD/ADHD are more likely to smoke than women without the disorder; therefore, a genetic link cannot be excluded.

The Centers for Disease Control and Prevention (CDC) quotes ADD/ADHD as one of the most prevalent childhood disorders affecting an estimated 6.4 million children (aged 4 to 17years) have been diagnosed in the US in 2011. The percentage of children with ADD/ADHD has increased from 7.8% in 2003 to 9.5% in 2007 to 11% in 2011 (CDC ADHD data and statistics, 2011). The incidence in adults with ADD/ADHD was reported as 4% to 5% in 2011 (Antshel et al. BMC Medicine 2011). The disorder is more prevalent in males, children, people with chronic health problems, dysfunctional families, and lower-income families.

Children and adults with ADD/ADHD are treated with the same medications. Parents of children aged 4 to 17 years diagnosed with ADD/ADHD reported that 6.1% were being treated with medications for the disorder in 2011 compared to 4.8% in 2007 (CDC ADHD: United States, 2003-2011). Effective behavior management techniques are also useful training techniques for children with ADD/ADHD (Antshel et al., 2011). Typical ADD/ADHD medications used to treat ADD/ADHD are categorized in one of four classes of medications: stimulants, (amphetamine or methylphenidate), nonstimulants (including some antihypertensives/central alpha-adrenergic agonists), antidepressants (tricyclics), and atypical antipsychotics. Typical medications used to treat ADD/ADHD currently on the market that are stimulants include amphetamine, dextroamphetamine mixed salts (Adderall®) and dextroamphetamine (Dexedrine®); typical methylphenidate stimulants include methylphenidate HCl (Ritalin®) and dexmethylphenidate (Focalin®); typical nonstimulants include atomoxetine HCl (Strattera®), guanfacine (Tenex® or Intuniv®), and clonidine (Catapres®); typical antidepressants include bupropion HCl (Wellbutrin®), venlafaxine (Effexor®), and imipramine (Tofranil®); and typical antipsychotics include aripiprazole (Abilify®).

Although there are a wide variety of medications to treat ADD/ADHD, there are some associated risks with some of the approved medications. The FDA has issued a warning about drug abuse with amphetamine stimulants. There is also a concern regarding the possibility that all amphetamine and methylphenidate stimulants used for ADD/ADHD may increase the risk of cardiac and psychiatric adverse events. The antidepressants used to treat ADD/ADHD have shown an increased risk of suicide in adults, especially in the first 1-2 months of treatment (Grohol, J., 2007).

Only 25% of children treated with medications for ADD/ADHD have a modest improvement (Antshel et al. BMC Medicine 2011). There is also a challenge in optimizing the benefit/risk ratio of treatment with careful adjustment of dosages and combined therapy for comorbid conditions, such as depression (Martin, B., 2007). Even with the knowledge gained to date regarding the disorder and the medications available, the disorder is difficult to treat effectively. There is poor compliance to treatment and the psychiatric comorbidities that complicate successful outcomes for patients with ADD/ADHD.

There is a need for a new drug with an acceptable efficacy and reduced adverse effects than the currently available therapies for treating ADD/ADHD.

REFERENCES

1. American Psychiatric Association: Diagnostic and Statistical Manual of Mental Disorders, 5th edition. Arlington, Va., American Psychiatric Association, 2013.
2. Antshel K M, Hargrave T M, Simonescu M, Kaul P, Hendricks K, Faraone S V. Advances in understanding and treating ADHD. Antshel et al. BMC Medicine 2011, 9:72, from www.biomedcentral.com/1741-7015/9/72.
3. Centers for Disease Control and Prevention. ADHD, data and statistics. 2011. Retrieved Mar. 27, 2014, from www-.cdc.gov/ncbddd/adhd/data.html
4. Centers for Disease Control and Prevention. Key Findings: Trends in the Parent-Report of Health Care Provider-Diagnosis and Medication Treatment for ADHD: United States, 2003-2011.
5. Di Pietro, N C, Seamans, J K. Dopamine and serotonin interactions in the prefrontal cortex: insights on antipsychotic drugs and their mechanism of action. Pharmacopsychiatry 2007 December; 40(S1), S27-S33. doi: 10.1055/s-2007-992133.
6. Findling R L, Short E J, Leskovec T, Townsend L D, Demeter C A, McNamara N K, Stansbrey R J. Aripiprazole in children with attention-deficit/hyperactivity disorder. J Child Adolesc Psychopharmacol. 2008 August; 18(4):347-54. doi: 10.1089/cap.2007.0124.
7. Grohol, J. Symptoms of Attention Deficit Hyperactivity Disorder (ADHD). Psych Central. 2007. Retrieved on Mar. 27, 2014, from psychcentral.com/lib/symptoms-of-attention-deficit-disorder-adhd/0001200.
8. Kinman T. ADHD and ADD: Differences, Types, Symptoms, and Severity, (medically reviewed by G Krucik). Healthline.
9. Martin B. Problems Related to ADHD. Phych Central. 2007. Retrieved on Mar. 27, 2014, from psychcentral.com/lib/problems-related-to-adhd/0001201.

DETAILED DESCRIPTION OF THE INVENTION

Definitions

"Alkyl" or "alkanyl" refers to a saturated, branched or straight-chain or cyclic monovalent hydrocarbon radical derived by the removal of one hydrogen atom from a single carbon atom of a parent alkane. Typical alkyl groups include, but are not limited to methyl; ethyl; propyls such as propan-1-yl, propan-2yl, cyclopropan-1-yl; butyls such as butan-1-yl, butan-2-yl, 2-methyl-propan-1-yl, 2-methyl-propan-2-yl, cyclobutan-1-yland the like. Preferably, an alkyl group comprises from 1-20 carbon atoms, more preferably, from 1 to 10, or 1 to 6, or 1-4 carbon atoms.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methy-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien 1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to formyl, acetyl, cyclohexylcarbonyl, cyclohexylmethylcarbonyl, benzoyl, benzylcarbonyl and the like.

"Acyloxyalkyloxycarbonyl" refers to a radical —C(O)OCR'R"OC(O)R'" where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$OC(O)CH$_3$, —C(O)OCH$_2$OC(O)CH$_2$CH$_3$, —C(O)OCH(CH$_3$)OC(O)CH$_2$CH$_3$, —C(O)OCH(CH$_3$)OC(O)C$_6$H$_5$ and the like.

"Acylalkyloxycarbonyl" refers to a radical —C(O)OCR'R"C(O)R'" where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$C(O)CH$_3$, —C(O)OCH$_2$C(O)CH$_2$CH$_3$, —C(O)OCH(CH$_3$)C(O)CH$_2$CH$_3$, —C(O)OCH(CH$_3$)C(O)C$_6$H$_5$ and the like.

"Acyloxyalkyloxycarbonylamino" refers to a radical —NRC(O)OCR'R"OC(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$OC(O)CH$_3$, —NHC(O)OCH$_2$OC(O)CH$_2$CH$_3$, —NHC(O)OCH(CH$_3$)OC(O)CH$_2$CH$_3$, —NHC(O)OCH(CH$_3$)OC(O)C$_6$H$_5$ and the like.

"Acylalkyloxycarbonylamino" refers to a radical —NRC(O)OCR'R"C(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$C(O)CH$_3$, —NHC(O)OCH$_2$C(O)CH$_2$CH$_3$, —NHC(O)OCH(CH$_3$)C(O)CH$_2$CH$_3$, —NHC(O)OCH(CH$_3$)C(O)C$_6$H$_5$ and the like.

"Acylamino" refers to "amide" as defined herein.

"Alkylamino" means a radical —NHR where R represents an alkyl, or cycloalkyl group as defined herein that may be optionally substituted by one or more substituents as defined herein. Representative examples include, but are not limited to, methylamino, ethylamino, 1-methylethylamino, cyclohexylamino and the like.

"Alkoxy" refers to a radical —OR where R represents an alkyl, or cycloalkyl group as defined herein that may be optionally substituted by one or more substituents as defined herein. Representative examples include, but are not limited to methoxy, ethoxy, propoxy, butoxy, cyclohexyloxy and the like.

"Alkoxycarbonyl" refers to a radical —C(O)-alkoxy where alkoxy is as defined herein.

"Alkoxycarbonylalkoxy" refers to a radical-OCR'R"C(O)-alkoxy where alkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_3$, —OCH$_2$C(O)OCH$_2$CH$_3$, —OCH(CH$_3$)C(O)OCH$_2$CH$_3$, —OCH(C$_6$H$_5$)C(O)OCH$_2$CH$_3$, —OCH(CH$_2$C$_6$H$_5$)C(O)OCH$_2$CH$_3$, —OC(CH$_3$)(CH$_3$)C(O)OCH$_2$CH$_3$, and the like.

"Alkoxycarbonylalkylamino" refers to a radical —NRCR'R"C(O)-alkoxy where alkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_3$, —N(CH$_3$)CH$_2$C(O)OCH$_2$CH$_3$, —NHCH(CH$_3$)C(O)

OCH$_2$CH$_3$, —NHCH(C$_6$H$_5$)C(O)OCH$_2$CH$_3$, —NHCH(CH$_2$C$_6$H$_5$)C(O)OCH$_2$CH$_3$, —NHC(CH$_3$)(CH$_3$)C(O)OCH$_2$CH$_3$, and the like.

"Alkylsulfonyl" refers to a radical —S(O)$_2$R where R is an alkyl, or cycloalkyl group as defined herein that may be optionally substituted by one or more substituents as defined herein. Representative examples include, but are not limited to, methylsulfonyl, ethylsulfonyl, propylsulfonyl, butylsulfonyl, and the like.

"Alkylsulfinyl" refers to a radical —S(O)R where R is an alkyl, or cycloalkyl group as defined herein that may be optionally substituted by one or more substituents as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined/herein that may be optionally substituted by one or more substituents as defined herein. Representative examples include, but are not limited to methylthio, ethylthio, propylthio, butylthio, and the like.

"Amide" or "acylamino" refers to a radical —NR'C(O)R", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, formylamino acetylamino, cyclohexylcarbonylamino, cyclohexylmethylcarbonyl-amino, benzoylamino, benzylcarbonylamino and the like.

"Aryl" refers to a monovalent aromatic hydrocarbon radical derived by the removal of one hydrogen atom from a single carbon atom of a parent aromatic ring system. Typical aryl groups include, but are not limited to, groups derived from benzene, naphthalene, and the like. Preferable, an aryl group comprises from 6 to 20 carbon atoms, more preferably, between 6 to 12 carbon atoms.

"Arylalkyl" refers to an acyclic alkyl in which one of the hydrogen atoms bonded to a carbon atom, typically a terminal or sp$^3$ carbon atom, is replaced with an aryl group. Typically arylalkyl groups include, but not limited to, benzyl, 2-phenylethan-1-yl, naphthylmethyl, 2-naphthylethan-1-yl, naphthobenzyl, 2-naphthophenylethan-1-yl and the like. Preferably, an arylalkyl group is (C$_6$-C$_{30}$)arylalkyl, e.g., the alkyl moiety of the arylalkyl group is (C$_1$-C$_{10}$) and the aryl moiety is (C$_6$-C$_{20}$), more preferably, an arylalkyl group is (C$_6$-C$_{20}$) arylalkyl, e.g., the alkyl moiety of the arylalkyl group is (C$_1$-C$_8$) and the aryl moiety is (C$_6$-C$_{12}$).

"Arylalkoxy" refers to an —O-arylalkyl radical where arylalkyl is as defined herein that may be optionally substituted by one or more substituents as defined herein.

"Arylalkoxycarbonylalkoxy" refers to a radical —OCR'R"C(O)-arylalkoxy where arylalkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_2$C$_6$H$_5$, —OCH(CH$_3$)C(O)OCH$_2$C$_6$H$_5$, —OCH(C$_6$H$_5$)C(O)OCH$_2$C$_6$H$_5$, —OCH(CH$_2$C$_6$H$_5$)C(O)O CH$_2$C$_6$H$_5$, —OC(CH$_3$)(CH$_3$)C(O)OCH$_2$C$_6$H$_5$, and the like.

"Arylalkoxycarbonylalkylamino" refers to a radical —NRCR'R"C(O)-arylalkoxy where arylalkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_2$C$_6$H$_5$, —N(CH$_3$)CH$_2$C(O)OCH$_2$C$_6$H$_5$, —NHCH(CH$_3$)C(O)OCH$_2$C$_6$H$_5$, —NHCH(C$_6$H$_5$)C(O)OCH$_2$C$_6$H$_5$, —NHCH(CH$_2$C$_6$H$_5$)C(O)OCH$_2$C$_6$H$_5$, —NHC(CH$_3$)(CH$_3$)C(O)OCH$_2$C$_6$H$_5$, and the like.

"Aryloxycarbonyl" refers to radical —C(O)—O-aryl where aryl is defined herein that may be optionally substituted by one or more substituents as defined herein.

"Aryloxycarbonylalkoxy" refers to a radical-OCR'R"C(O)-aryloxy where aryloxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OC$_6$H$_5$, —OCH(CH$_3$)C(O)OC$_6$H$_5$, —OCH(C$_6$H$_5$)C(O)OC$_6$H$_5$, —OCH(CH$_2$C$_6$H$_5$)C(O)OC$_6$H$_5$, —OC(CH$_3$)(CH$_3$)C(O)OC$_6$H$_5$, and the like.

"Aryloxycarbonylalkylamino" refers to a radical —NRCR'R"C(O)-aryloxy where aryloxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OC$_6$H$_5$, —N(CH$_3$)CH$_2$C(O)OC$_6$H$_5$, —NHCH(CH$_3$)C(O)OC$_6$H$_5$, —NHCH(C$_6$H$_5$)C(O)OC$_6$H$_5$, —NHCH(CH$_2$C$_6$H$_5$)C(O)OC$_6$H$_5$, —NHC(CH$_3$)(CH$_3$)C(O)OC$_6$H$_5$, and the like.

"Carbamoyl" refers to the radical —C(O)NRR where each R group is independently, hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methylcarbamate (—NHC(O)OCH$_3$), ethylcarbamate (—NHC(O)OCH$_2$CH$_3$), benzylcarbamate (—NHC(O)OCH$_2$C$_6$H$_5$), and the like.

"Carbonate" refers to a radical —OC(O)OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methyl carbonate (—C(O)OCH$_3$), cyclohexyl carbonate (—C(O)OC$_6$H$_{11}$), phenyl carbonate (—C(O)OC$_6$H$_5$), benzyl carbonate (—C(O)OCH$_2$C$_6$H$_5$), and the like.

"Cycloalkyl" refers to a substituted or unsubstituted cylic alkyl radical. Typical cycloalkyl groups include, but are not limited to, groups derived from cyclopropane, cyclobutane, cyclopentane, cyclohexane, and the like. In a preferred embodiment, the cycloalkyl group is (C$_3$-C$_{10}$) cycloalkyl, more preferably (C$_3$-C$_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkoxycarbonyl" refers to a radical —C(O)—OR where R is cycloheteroalkyl as defined herein that may be optionally substituted by one or more substituents as defined herein.

"Dialkylamino" means a radical —NRR' where R and R' independently represent an alkyl or cycloalkyl group as defined herein that may be optionally substituted by one or more substituents as defined herein. Representative examples include, but are not limited to dimethylamino, methylethylamino, di-(1-methylethyl)amino, (cyclohexyl)(methyl)amino, (cyclohexyl)(ethyl)amino, (cyclohexyl)(propyl)amino, and the like.

"Ester" refers to a radical —C(O)OR, where R is alkyl, substituted alkyl, cycloalkyl, substituted cycloalkyl, cycloheteroalkyl, substituted cycloheteroalkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl as defined herein that may be optionally substituted by one or more substituents as defined herein. Representative examples include, but are not limited to, methyl ester (—C(O)OCH$_3$), cyclohexyl ester (—C(O)OC$_6$H$_{11}$), phenyl ester (—C(O)OC$_6$H$_5$), benzyl ester (—C(O)OCH$_2$C$_6$H$_5$), and the like.

"Ether" refers to a radical —OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Halogen" means fluoro, chloro, bromo, or iodo.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined that may be optionally substituted by one or more substituents as defined herein.

"Heteroarylalkyl" refers to an acyclic alkyl radical in which one of the hydrogen atoms bonded to a carbon atom, typically a terminal or sp3 carbon atom, is replaced with a heteroaryl group. Preferably, the heteroarylalkyl radical is a 6-30 carbon membered heteroarylalkyl, e.g., the alkyl moiety of the heteroarylalkyl is 1-10 membered and the heteroaryl moiety is a 5-20 membered heteroaryl, more preferably, a 6-20 membered heteroarylalkyl, e.g., the alkyl moiety of the heteroarylalkyl is 1-8 membered and the heteroaryl moiety is a 5-12 membered heteroaryl.

"Oxo" means the divalent radical=O.

"Pharmaceutically acceptable" means approved or approvable by a regulatory agency of the Federal or state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, succinic acid, maleic acid, fumaric acid, tartaric acid, citric acid, cinnamic acid, methanesulfonic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Phosphate" refers to a radical —OP(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Phosphonate" refers to a radical —P(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Preventing" or "Prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Racemate" refers to an equimolar mixture of enantiomers of a chiral molecule.

"Substituted" refers to a group in which one or more hydrogen atoms are each independently replaced with the same or different substituents(s). Typical substituents include, but are not limited to, —X, —R$^{54}$, —O$^-$, =O, —OR$^{54}$, —SR$^{54}$, —S$^-$, =S, —NR$^{54}$R$^{55}$, =NR$^{54}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$OR$^{54}$, —OS(O)$_2$O$^{31}$, —OS(O)$_2$R$^{54}$, —P(O)(O—)$_2$, —P(O)(OR$^{14}$)(O$^{31}$), —OP(O)(OR$^{54}$)(OR$^{55}$), —C(O)R$^{54}$, —C(S)R$^{54}$, —C(O)OR$^{54}$, —C(O)NR$^{54}$R$^{55}$, —C(O)O$^-$, —C(S)OR$^{54}$, —NR$^{56}$C(O)NR$^{54}$R$^{55}$, —NR$^{56}$C(S)NR$^{54}$R$^{55}$, —NR$^{57}$C(NR$^{56}$)NR$^{54}$R$^{55}$, and —C(NR$^{56}$)NR$^{54}$R$^{55}$, where each X is independently a halogen; each R$^{54}$, R$^{55}$, R$^{56}$ and R$^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{58}$R$^{59}$, —C(O)R$^{58}$ or —S(O)$_2$R$^{58}$ or optionally R$^{58}$ and R$^{59}$ together with the atom to which they are both attached form a cycloheteroalkyl or substituted cycloheteroalkyl ring; and R$^{58}$ and R$^{59}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonamide" refers to a radical —S(O)(O)NR'R", where R' and R" are independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein or optionally R' and R" together with the atom to which they are both attached form a cycloheteroalkyl or substituted cycloheteroalkyl ring. Representative examples include but not limited to azetidinyl, pyrrolidinyl, piperidinyl, morpholinyl, 4-(NR''')-piperazinyl or imidazolyl group wherein said group may be optionally substituted by one or more substituents as defined herein. R''' hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonate" refers to a radical —S(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Thio" means the radical —SH.

"Thioether" refers to a radical —SR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Treating" or "Treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically (e.g., stabilization of a discernible symptom), physiologically, (e.g., stabilization of a physical parameter), or both.

"Therapeutically effective amount" means the amount of a compound that, when administered to a patient for treating a disease, is sufficient to effect such treatment for the disease. The "therapeutically effective amount" will vary depending on the compound, the disease and is severity and the age, weight, etc., of the patient to be treated, and can be determined by one of skill in the art without undue experimentation.

The present invention is directed to a method for treating attention deficit disorder (ADD)/attention deficit hyperactivity disorder (ADHD) by administering a compound of Formula I to a patient. The terms of ADD and ADHD can be used interchangeably. ADHD is a neuropsychiatric disease/disorder, which is caused by the imbalance of key neurochemicals dopamine and serotonin in the brain. Compounds of Formula I have potent binding affinities at the dopamine and serotonin receptors. In addition, Compounds of Formula I exhibit potent binding affinity with partial agonist activity at the dopamine ($D_2$, $D_3$ and D4) and serotonin (5-$HT_{1A}$ and 5-$HT_{2A}$) receptors, and antagonist activity at the serotonin 5-$HT_{2B}$, 5-$HT_6$ and 5-$HT_7$ receptors. The partial agonist activities for these key highly expressed receptors in the brain cause dopamine-serotonin stabilizing effect in the brain.

The inventor has discovered that compounds of Formula I, which has Dopamine $D_4$ receptor antagonist activity, prevents stress induced cognitive deficits (see Dopamine $D_4$ receptor antagonist effect in Arnsten, A. F. T., et al, Neuropsychopharmacology 2000, 23: 405-410). The inventor has discovered that compounds of Formula I, which has serotonin 5-$HT_{2B}$ receptor antagonist activity, improves cognition and ameliorate ADHD symptoms (see 5-$HT_{2B}$ receptor antagonist effect in Manor, I., et al, J Clin Psychiatry 2012, 73:1517-1523). The inventor has further discovered that compounds of Formula I, which has serotonin 5-$HT_7$ receptor antagonist activity, improves cognition and behavioral symptoms (see 5-$HT_{2B}$ receptor antagonist effect in Waters, K. A. et al, Behavioral Research 2012, 228:211-218).

ADHD has been conceptualized in relation to varying cognitive problems including attention, reward response, executive functioning, and other cognitive processes. By blocking key dopamine ($D_2$, $D_3$ and $D_4$) receptors and serotonin (5-$HT_{1A}$ and 5-$HT_{2A}$, 5-$HT_{2B}$, 5-$HT_6$ and 5-$HT_7$) receptors, compounds of Formula I improve the comorbid major conditions of ADHD such as cognition impairment and some of the behavioral symptoms.

Compounds Useful in the Invention

Compounds of Formula (I) are useful for the present invention:

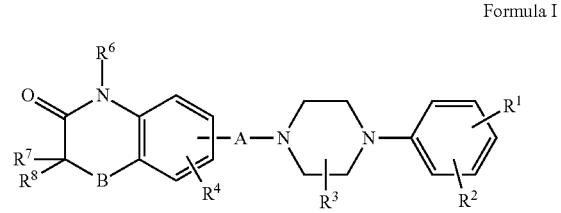

Formula I wherein:

A is —$(CH_2)_n$—, —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, $(CH_2)_n$—NH—C(O)—$CH_2$—$CH_2$—, or $(CH_2)_n$—S—C(O)—$CH_2$—$CH_2$—, wherein n is an integer from 1 to 7;

B is O, S, S(O)(O), or $NR^5$; and each of $R^1$, $R^2$, $R^3$, $R^4$, $R^5$, $R^6$, $R^7$, and $R^8$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide, wherein $R^1$, $R^2$, $R^3$, $R^4$, $R^5$, $R^6$, $R^7$ and $R^8$ and A may optionally be substituted with isotopes that include, but not limited to $^2H$ (deuterium), $^3H$ (tritium), $^{13}C$, $^{36}Cl$, $^{18}F$, $^{15}N$, $^{17}O$, $^{18}O$, $^{31}P$, $^{32}P$, and $^{35}S$; with $^2H$ (deuterium) being preferred;

or a pharmaceutically acceptable salt, racemate or diastereomeric mixtures thereof.

In one embodiment, compounds of Formula I has the structure of Formula Ia:

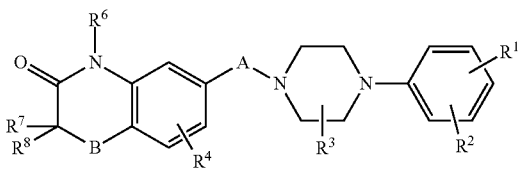

Formula Ia

In another aspect of the invention, A is —$(CH_2)_n$—.

In another aspect of the invention, A is —O—$(CH_2)_n$—, —S—$(CH_2)_n$—, —$CH_2$O—$(CH_2)_n$—, —$(CH_2)_n$—O—$CH_2$—$CH_2$—, —$CH_2$—S—$(CH_2)_n$—, or —$(CH_2)_n$—S—$CH_2$—$CH_2$—; with A being —O—$(CH_2)_n$— preferred.

In another aspect of the invention, A is —NH—C(O)—$(CH_2)_n$—, —$CH_2$—NH—C(O)—$(CH_2)_n$—, —$CH_2$—C(O)—NH—$(CH_2)_n$— or —$(CH_2)_n$—C(O)—NH—$CH_2$—$CH_2$—.

In another aspect of the invention, B is O.

In another aspect of the invention, $R^3$, $R^4$, $R^6$, $R^7$, and $R^8$ are H.

In another aspect of the invention, each of $R^1$ and $R^2$ is independently H, halogen, haloalkyl or alkoxy.

In a preferred embodiment, A is —O—$(CH_2)_n$—, n=2-5; B is O; $R^3$, $R^4$, $R^6$, $R^7$, and $R^8$ are H; and $R^1$ and $R^2$ is independently H, halogen, haloalkyl or alkoxy.

Preferred compounds of Formula I include, for example,

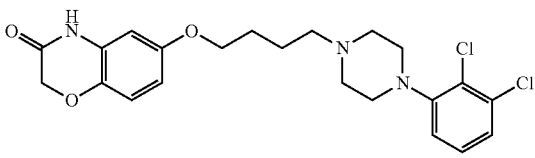 [SMILES: O=C1COc2ccc(OCCCCN3CCN(c4cccc(Cl)c4Cl)CC3)cc2N1]

6-(4-(4-(2,3-dichlorophenyl)piperazin-1-yl)butoxy)-2H-benzo[b][1,4]oxazin- -3(4H)-one, and its hydrochloride salt; and

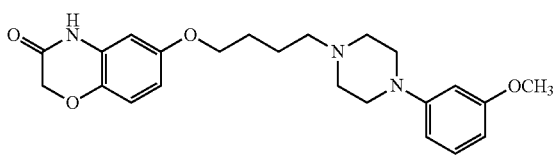 [SMILES: COc1cccc(N2CCN(CCCCOc3ccc4c(c3)NC(=O)CO4)CC2)c1]

6-(4-(4-(2-methoxyphenyl)piperazin-1-yl)butoxy)-2H-benzo[b][1,4]oxazin-3-(4H)-one, and its hydrochloride.

The compounds useful for this invention have one or more of the following characteristics or properties:
(a) Compounds of the invention can have affinity for dopamine $D_2$ receptors;
(b) Compounds of the invention can have affinity for serotonin $D_4$ receptors;
(c) Compounds of the invention can have affinity for serotonin 5-$HT_{1A}$ receptors;
(d) Compounds of the invention can have affinity for serotonin 5-$HT_{2A}$ receptors;
(e) Compounds of the invention can have affinity for serotonin 5-$HT_{2B}$ receptors;
(f) Compounds of the invention can have affinity for serotonin 5-$HT_7$ Receptors.

The compounds useful for the present invention further pertain to enantiomerically isolated compounds of Formula I. The isolated enantiomeric forms of the compounds of Formula I are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. Thus, for example, the compounds are at least about 90% enantiomeric excess, preferably at least about 95% enantiomeric excess, more preferably at least about 97% enantiomeric excess, or even more preferably, at least 99% or greater than 99% enantiomeric excess.

Formula I compounds can be synthesized according U.S. Pat. No. 8,188,076, which is incorporated herewith in its entirety.

Method of Treating ADD/ADHD

The present invention is directed to a method for treating attention deficit disorder (ADD) and/or attention deficit hyperactivity disorder (ADHD). The method comprises the step of administering an effective amount of compound of Formula I to a patient who is suffering from ADHD.

The present invention ameliorates at least one clinical symptom and/or at least one physical parameter associated with ADHD. The treated patients improve ADHD rating scale IV (ARS-IV), ADHD self-report scale (ASRS), clinical global impression (CGI), and/or cognitive functions.

ADHD rating scale IV (ARS-IV) rates the following behaviors: 1. Fails to give close attention to details or makes careless mistakes in work. 2. Fidgets with hands or feet or squirms in seat. 3. Has difficulty sustaining attention in tasks or play activities. 4. Leaves seat in situations in which remaining seated is expected. 5. Does not seem to listen when spoken to directly. 6. Runs about or climbs excessively in situations in which it is inappropriate. 7. Does not follow through on instructions and fails to finish work. 8. Has difficulty playing or engaging in leisure activities quietly. 9. Has difficulty organizing tasks and activities. 10. Is "on the go" or acts as if "driven by a motor." 11. Avoids tasks that require sustained mental effort. 12. Talks excessively. 13. Loses things necessary for tasks or activities. 14. Blurts out answers before questions have been completed. 15. Is easily distracted. 16. Has difficulty awaiting turn. 17. Is forgetful in daily activities. 18. Interrupts or intrudes on others.

Kessler et al (*Psychological Medicine*, 35:245-256, 2005) report the WHO adult ADHD self-report scale (ASRS), for use in the general population. The ASRS Symptom Checklist is a self-reported questionnaire used to assist in the diagnosis of adult ADHD.

The clinical global impression-improvement scale (CGI-I) is a 7 point scale that requires the clinician to assess how much the patient's illness has improved or worsened relative to a baseline state at the beginning of the intervention, and rated as: 1, very much improved; 2, much improved; 3, minimally improved; 4, no change; 5, minimally worse; 6, much worse; or 7, very much worse.

When used to treat ADHD, one or more compound of Formula I can be administered alone, or in combination with other agents, to a patient. The patient may be an animal, preferably a mammal, and more preferably a human.

Formula I compounds are preferably administered orally. Formula I compounds may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravabinal, transdermal, rectally, by inhalation, or topically, particularly to the ears, nose, eyes or skin. Transdermal administration may be preferred for young children.

Formula I compounds can be delivered via sustained release systems, preferably oral sustained release systems. In one embodiment, a pump may be used (see, Langer, supra; Sefton, 1987, CRC Crit. Ref Biomed. Eng. 14:201; Saudek et al., 1989, N. Engl. J. Med. 321:574).

In one embodiment, polymeric materials can be used (see "Medical Applications of Controlled Release," Langer and Wise (eds.), Wiley, New York (1984); Ranger and Peppas, 1983, J. Macromol. Sci. Rev. Macromol Chem. 23:61; see also Levy et al., 1985, Science 228:190; During et al., 1989, Ann. Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described in the art (Bamba et al., Int. J. Pharm., 1979, 2, 307).

In one embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time controlled release), polymers that are degraded by enzymes (i.e., enzyme controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In a preferred embodiment, OROS® osmotic delivery systems are used for oral sustained release delivery devices (See for example, Theeuwes et al., U.S. Pat. No. 3,845,770; and Theeuwes et al, U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, Science 249:1527-1533 may also be used.

Formula I compounds may be cleaved either chemically and/or enzymatically. One or more enzymes present in the stomach, intestinal lumen, intestinal tissue, blood, liver, brain or any other suitable tissue of a mammal may enzymatically cleave the compounds and/or compositions of the invention.

Pharmaceutical Formulation of the Invention

The present pharmaceutical formulation contains a therapeutically effective amount of one or more compounds of Formula I, preferably in purified form, together with a suitable amount of a pharmaceutically acceptable vehicle. When administered to a patient, the pharmaceutical formulation is preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making levigating, and emulsifying, encapsulating, entrapping or lyophilizing process. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, and capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 17$^{th}$ Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about mM to about 50 mM) etc. Additionally, flavoring agents, preservatives, coloring agents, bile salts, acylcamitines and the like may be added.

Compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as alcohol, glycol, polyglycol or fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa, butter or other glycerides. In addition to the formulations described previously, a compound of the invention may also be formulated as depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

Dosage for the Treatment

The amount of Formula I compound administered is dependent on, among other factors, the subject being treated, and the weight of the subject, the severity of the affliction, the manner of administration and the judgment of the prescribing physician. For example, the dosage may be delivered in a pharmaceutical composition by a single administration, by multiple applications or controlled release. In one embodiment, the compounds of the invention are delivered by oral sustained release administration. In one embodiment, the compounds of the invention are administered twice per day, and preferably, once per day. Dosing may be repeated intermittently, may be provided alone or in combination with other drugs, and may continue as long as required for effective treatment of the disease state or disorder.

The compounds of Formula I may be administered in the range 0.1-500 mg, preferably 1-100, or 0.5-50 mg per day given in one or more doses. For example, the compounds are administered 1 mg, 5 mg, 10 mg, 15 mg, 20 mg, 25 mg, 35 mg or 50 mg per day. The actual dosage depends on the age and body weight of the subject. In general, under the age group 12 years, the daily dosage is between 0.5 to 2.5 mg. Between the age group of 12-18 years, the daily dosage is 2.5 to 5 mg. Above the age group 18 years, the daily dosage is 5 to 50 mg.

Combination Therapy

In certain embodiments of the present invention, the compounds of the invention can be used in combination therapy with at least one other therapeutic agent. Formula I compounds and the therapeutic agent can act additively or synergistically. In one embodiment, Formula I compound is administered concurrently with the administration of another therapeutic agent, which can be part of the same composition of Formula I compound. In another embodiment, a composition comprising a compound of the invention is administered prior or subsequent to administration of another therapeutic agent.

The invention is further illustrated by the following examples.

EXAMPLES

Example 1

In Vitro Pharmacology Results

Two arylpiperazine derivatives of Formula (I) were tested in the in vitro pharmacological assays to evaluate their activities for dopamine $D_2$ and $D_4$, and serotonin 5-$HT_{1A}$, 5-$HT_{2A}$, 5-$HT_{2B}$, 5-$HT_6$ and 5-$HT_7$ receptors.

Methods employed to evaluate the test compounds A and B in radioligand binding assays were adopted from the scientific literature references as shown in Table 1 to maximize reliability and reproducibility. Reference standards were run as an integral part of each assay to ensure the validity of the results obtained. Ki values were calculated using the equation of Cheng and Prusoff (Cheng, Y., Prusoff, W. H. Biochem Pharmacol 1973, 22:3099-3108).

Compound A=6-(4-(4-(2-methoxyphenyl)piperazin-1-yl)butoxy)-2H-benzo[b][1,4]oxazin-3-(4H)-one hydrochloride.

Compound B=6-(4-(4-(2,3-dichlorophenyl)piperazin-1-yl)butoxy)-2H-benzo[b][1,4]oxazin-3(4H)-one hydrochloride.

TABLE 1

| Compound | Assay | Ki (nM) | Reference |
| --- | --- | --- | --- |
| A | $D_{2S}$ | 0.30 | 1 |
| A | 5-$HT_{1A}$ | 0.65 | 2 |
| B | $D_{2L}$ | 0.45 | 3 |
| B | $D_{2S}$ | 0.26 | 4 |
| B | $D_{4.4}$ | 6.0 | 5 |
| B | 5-$HT_{1A}$ | 1.5 | 2 |
| B | 5-$HT_{2A}$ | 2.5 | 4 |
| B | 5-$HT_{2B}$ | 0.19 | 6 |
| B | 5-$HT_6$ | 51 | 7 |
| B | 5-$HT_7$ | 2.7 | 8, 9 |

Literature References in Table 1:
1. Gundlach, A. L., et al., Life Sciences 1984, 35:1981-1986.
2. Hoyer, D., et al, Eur J Pharmacol, 1985, 118:13-23
3. Hall, D. a., et al, Brit J Pharmacol, 1997, 121:731-736.
4. Carpenter, J. W., et al, (2002) Configuring radioligand receptor binding assays for HTS using scintillation proximity assay technology. Methods in Molecular Biology 190 High Throughput Screening: Methods and Protocols
[www.ncgc.nihgov/guidance/manualtoc.html]
5. Van Tol, et al, nature 1992, 358:149-152.
6. Bonhaus, D. W., et al, Brit J Pharmacol, 1995, 115: 622-628.
7. Monsma, F. J., et al, Mol Pharmacol, 1993, 43:320-327.
8. Shen, Y. et al, J. Biol Chem, 1993, 268:18200-18204.
9. Adham, N., et al, J Pharmacol Exp Ther, 1998, 287: 508-514.

Table 1 shows that both Compounds A and B have strong activities for pharmacological blockade of key dopamine ($D_2$ and $D_4$) receptors and serotonin (5-$HT_{1A}$ and 5-$HT_{2A}$, 5-$HT_{2B}$, 5-$HT_6$ and 5-$HT_7$) receptors, and therefore, they are expected to be effective for the treatment of ADHD, especially comorbid major conditions such as cognition impairment and some of the behavioral symptoms.

Example 2

Treatment of ADHD in Adolescents and Adults

Objective: This is a prospective, open-label, 6-week study of Compound B, 6-(4-(4-(2,3-dichlorophenyl)piperazin-1-yl)butoxy)-2H-benzo[b][1,4]oxazin-3(4H)-one hydrochloride, in outpatient children, adolescents and adults with a primary diagnosis of ADHD and free of other major psychopathology. The six-week treatment phase is proceeded by a 1-3 week screening phase.

Patient Inclusion Criteria
Patients meet all of the following inclusion criteria:
1. Outpatients, children, adolescents and adults (inclusive);
2. Currently meets DSM-IV (American Psychiatric Association, 1994) criteria for a primary diagnosis of ADHD (either predominantly inattentive type or combined type) based on the results of semi-structured diagnostic assessment (K-SADS-PL)(Kaufman et al., 1997) and based on the results of a clinical interview with a child and adolescent psychiatrist;
3. Patients, who in the investigator's opinion, have substantial symptoms of ADHD for which pharmacotherapy is indicated;
4. Has provided written informed assent to participate in this study.

Patient Exclusion Criteria
Patients do not meet any of the following exclusion criteria:
1. Patients who have a history of allergy or hypersensitivity intolerance to Compound B;
2. Patients with an active or prior neurological/medical disorder for which treatment with Compound B would be contraindicated (such as tardive dyskinesia or neuroleptic malignant syndrome);
3. Patients with clinical evidence of autistic disorder, Rett's syndrome or Asperger's syndrome;
4. Patients with any bipolar spectrum disorder;
5. Patients with any schizophrenia spectrum disorder;
6. Patients with conduct disorder;
7. Patients with post-traumatic stress disorder or generalized anxiety disorder;
8. Patients with a substance abuse disorder;
9. Females who are sexually active, pregnant or lactating;
10. Patients with a suicide attempt requiring medical/psychiatric care within the past 6 months;
11. Patient taking psychotropic agents within one week of baseline (3 days for psychostimulants, 2 weeks for fluoxetine);
12. Patients with evidence of mental retardation (I.Q.<70) based on the results of the Peabody Picture Vocabulary Test-III (PPVT-III)(Dunn and Dunn, 1981);
13. Patients who have a general medical or neurological condition that could interfere with the interpretation of the clinical response to Compound B treatment;
14. Patients who are unable to swallow pills or capsules;
15. Patients for whom the need for hospitalization during the course of the study appears likely.

Test Compound: Compound B, 6-(4-(4-(2,3-dichlorophenyl)piperazin-1-yl)butoxy)-2H-benzo[b][1,4]oxazin-3(4H)-one hydrochloride, is formulated in the form of liquid, tablet, or capsule.

Placebo contains the same vehicle without the active compound.

Methodology: This is open-label, 6-week clinical activity study.

A total of 20-120 patients are enrolled; about ¾ of the patients are treated with Compound B, and ¼ of the patients are treated with placebo. The test compounds and the placebo are delivered either by oral administration or by transdermal patch for 6 weeks.

For oral administration, patients take 0.5-50 mg of test compound or placebo once a day.

For transdermal administration, doses that achieve similar blood concentration as that of effective oral doses are given to patients. The patches are replaced every week, every two weeks, or every 4 weeks.

Safety assessments and measures of ADHD symptomatology are collected prior to and during therapy, i.e., at baseline and Weeks 1, 2, 3, 4, and 6.

Criteria for Evaluation:
Safety:
Safety assessments and adverse events are monitored throughout the study.

Clinical Activity:
The clinical activity parameters are the measurement of ADHD rating scale IV (ARS-IV), clinical global impression (CGI), and cognitive measures.

Primary End Point: ARS-IV and CGI of treated patients are expected to be better than those of patients treated with placebo.

Secondary end point: Trail Making Test A and B of treated patients is expected to be better than those of patients treated with placebo.

While the invention has been particularly shown and described with reference to a preferred embodiment and various alternate embodiments, it will be understood by persons skilled in the relevant art that various changes in form and details can be made therein without departing from the scope of the invention. All printed patents and publications referred to in this application are hereby incorporated herein in their entirety by this reference.

What is claimed is:
1. A method of treating attention deficit hyperactivity disorder (ADHD), the method comprising administering to a patient in need thereof an effective amount of a compound of Formula 1:

Formula 1

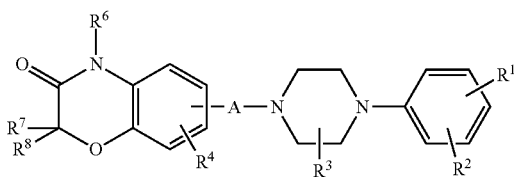

or a pharmaceutically acceptable salt, isomer, racemate, or diastereomeric mixture thereof, wherein:

A is —O—(CH$_2$)$_n$—, wherein n is an integer from 1 to 7; and

R$^1$, R$^2$, R$^3$, R$^4$, R$^6$, R$^7$, and R$^8$ are independently hydrogen, alkyl, substituted alkyl, aryl, substituted aryl, arylalkyl, substituted arylalkyl, cycloalkyl, substituted cycloalkyl, alkoxy, alkoxycarbonyl, alkylsulfinyl, alkylsulfonyl, alkylthio, amino, alkylamino, dialkylamino, arylalkoxy, carboxy, carbamoyl, carbamate, carbonate, cyano, halogen, or hydroxy; wherein the hydrogen of R$^1$, R$^2$, R$^3$, R$^4$, R$^6$, R$^7$ and R$^8$ and A are optionally substituted with $^2$H (deuterium).

2. The method according to claim 1, wherein R$^3$, R$^4$, R$^6$, R$^7$, and R$^8$ are hydrogen.

3. The method according to claim 1, wherein R$^4$ is H.

4. The method according to claim 1, wherein R$^1$ and R$^2$ are independently H, halogen, or alkoxy.

5. The method according to claim 4, wherein R$^1$ is H, and R$^2$ is methoxy.

6. The method according to claim 1, wherein R$^1$ and R$^2$ are chloro.

7. The method according to claim 1, wherein A is —O—(CH$_2$)$_n$—; and R$^3$, R$^4$, R$^6$, R$^7$, and R$^8$ are independently hydrogen or alkyl.

8. The method according to claim 7, wherein R$^3$, R$^4$, R$^6$, R$^7$, and R$^8$ are hydrogen.

9. The method according to claim 7, wherein R$^1$ is H, and R$^2$ is methoxy.

10. The method according to claim 7, wherein R$^1$ and R$^2$ are chloro.

11. The method according to claim 1, wherein the compound is 6-(4-(4-(2-methoxyphenyl)piperazin-1-yl)butoxy)-2H-benzo[b][1,4]oxazin-3-(4H)-one hydrochloride.

12. A method of treating attention deficit hyperactivity disorder (ADHD), comprising administering to a patient in need thereof an effective amount of 6-(4-(4-(2,3-dichlorophenyl)piperazin-1-yl)butoxy)-2H-benzo[b][1,4]oxazin-3(4H)-one hydrochloride, or a pharmaceutically acceptable salt, isomer, racemate, or diastereomeric mixture thereof.

13. The method according to claim 1, wherein the compound is in the form of a hydrochloride salt.

14. The method according to claim 1, wherein the compound is administered in a pharmaceutical composition comprising a pharmaceutically acceptable carrier, excipient, or diluent.

15. The method according to claim 1, wherein A is —O—(CH$_2$)$_n$—, n=2-5; R$^3$, R$^4$, R$^6$, R$^7$, and R$^8$ are H; and R$^1$ and R$^2$ is independently H, halogen, or alkoxy.

* * * * *